United States Patent [19]

Hewett et al.

[11] Patent Number: 5,264,411
[45] Date of Patent: Nov. 23, 1993

[54] HERBICIDAL METHOD COMPRISING THE USE OF DIFLUFENICAN

[75] Inventors: Richard H. Hewett, Thaxted; Ponnan Veerasekaran, Ongar both of England

[73] Assignee: May & Baker Limited, Dagenham, England

[21] Appl. No.: 798,961

[22] Filed: Nov. 27, 1991

Related U.S. Application Data

[63] Continuation of Ser. No. 447,507, Dec. 7, 1989, abandoned, which is a continuation of Ser. No. 887,725, Jul. 21, 1986, abandoned.

[30] Foreign Application Priority Data

Jul. 23, 1985 [GB] United Kingdom ............... 8518579
Oct. 10, 1985 [GB] United Kingdom ............... 8526734

[51] Int. Cl.$^5$ ............................................. A01N 43/40
[52] U.S. Cl. ..................................... 504/130; 504/141
[58] Field of Search .................... 71/94, 105; 504/130, 504/141

[56] References Cited

U.S. PATENT DOCUMENTS

| | | | |
|---|---|---|---|
| 3,397,054 | 8/1968 | Hart | 71/105 |
| 4,332,613 | 6/1982 | Esposito | 71/105 |

FOREIGN PATENT DOCUMENTS 2087887  6/1982  United Kingdom .

Primary Examiner—Glennon H. Hollrah
Assistant Examiner—Brian M. Burn
Attorney, Agent, or Firm—Burn, Doane, Swecker & Mathis

[57] ABSTRACT

The present invention relates to a method of controlling the growth of weeds at a cereal crop locus which comprises applying to the locus (a) bromoxynil, which is 3,5-dibromo-4-hydroxybenzonitrile, or ioxynil, which is 4-hydroxy-3,5-diiodobenzonitrile, an agriculturally acceptable salt or ester thereof or a mixture thereof and (b) diflufenican which is N-(2,4-difluorophenyl)-2-(3-trifluoromethylphenoxy)nicotinamide.

43 Claims, 1 Drawing Sheet

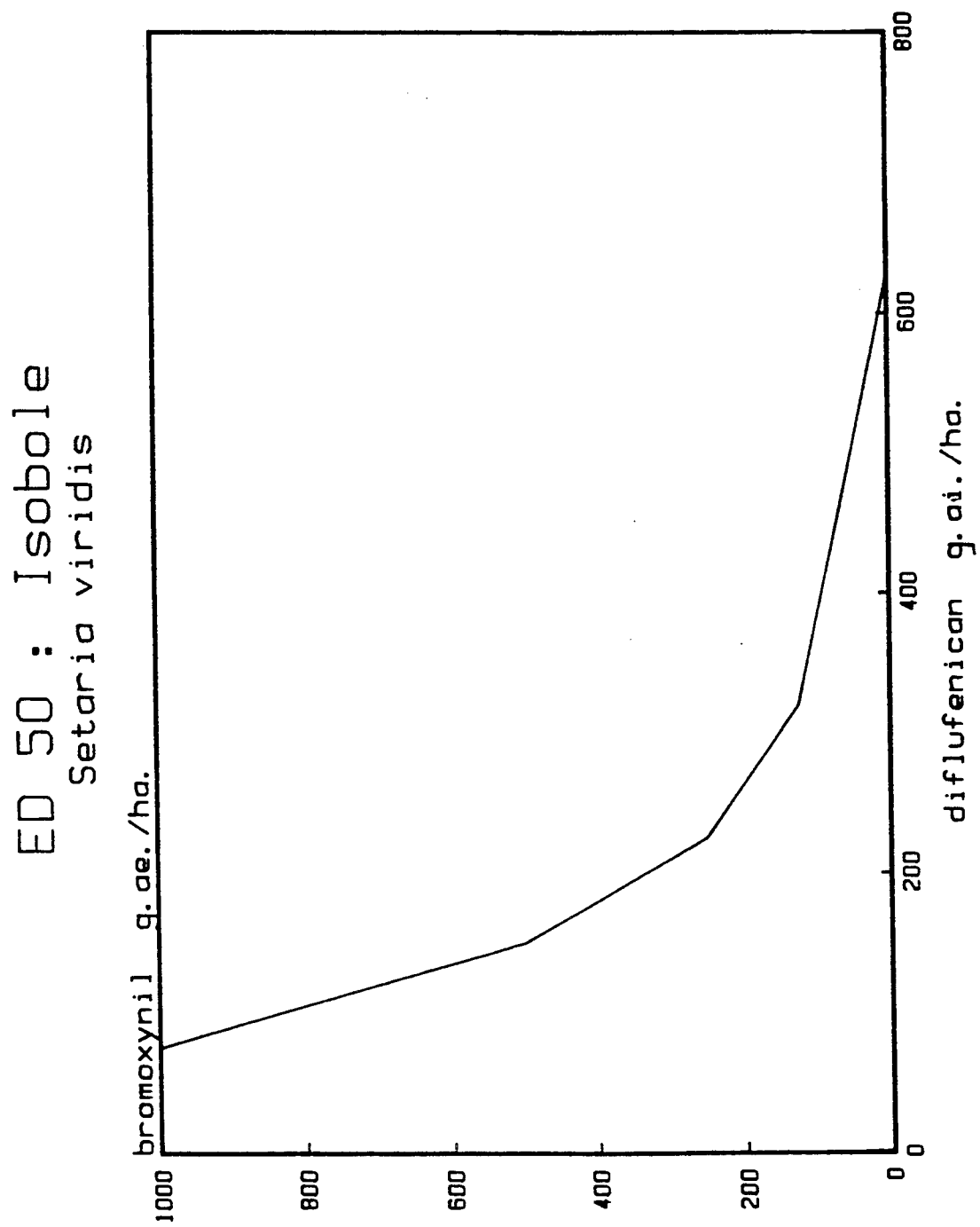
Figure (1)

HERBICIDAL METHOD COMPRISING THE USE OF DIFLUFENICAN

This application is a continuation of application Ser. No. 07/447,507, filed Dec. 7, 1989, now abandoned, which is a continuation of application Ser. No. 06/887,725, filed Jul. 21, 1986, now abandoned.

The present invention relates to new herbicidal compositions comprising N-(2,4-difluorophenyl)-2-(3-trifluoromethylphenoxy)nicotinamide of the formula depicted in FIG. 1 hereinafter, which is disclosed in the specification of British Patent Publication No. 2087887A as a pre- and/or post-emergence herbicide, and to their use in agriculture.

Bromoxynil [3,5-dibromo-4-hydroxybenzonitrile] and ioxynil [4-hydroxy-3,5-diiodobenzonitrile] and mixtures thereof are used on a large scale for post-emergence broad-leaf weed control in cereal crops. When used to control weeds at the "seedling" stage, to remove early competition, they are extremely effective, but owing to lack of residual activity in the soil they do not control the weeds which emerge after application. This can necessitate repeated application or delaying spraying until the majority of weeds have emerged by which time the oldest have exerted a considerable competitive effect on the crop. In addition certain broad-leaf weed species such as *Stellaria media, Galium aparine, Viola tricolor, Viola arvensis* and *Veronica hederifolia* are difficult to control with ioxynil and particularly with bromoxynil.

Bromoxynil and ioxynil and mixtures thereof also have no useful activity against annual grass weeds.

It is to be understood that where in this specification reference is made to a "HBN herbicide" it is intended to refer to bromoxynil [3,5-dibromo-4-hydroxybenzonitrile] or ioxynil [4-hydroxy-3,5-diiodobenzonitrile] in the form of the parent phenol (acid equivalent), an agriculturally acceptable salt or ester thereof, preferably a metal or amine salt or an ester thereof with an alkanoic acid containing from 2 to 10 carbon atoms, or to mixtures, preferably 3:1–1:3 wt/wt mixtures calculated in terms of acid equivalent weights, thereof where the context so permits.

As a result of research and experimentation it has been discovered that the use of the compound N-(2,4-difluorophenyl)-2-(3-trifluoromethylphenoxy)nicotinamide (hereinafter referred to for convenience as diflufenican) in combination with the HBN herbicide:

a) adds residual soil activity, allowing early application and removal of weed competition without the necessity of repeated application, b) widens the spectrum of weed control to include weeds such as *Stellaria media, Galium aparine* and *Viola arvensis*, and c) gives control of annual grass weeds such as *Alopecurus myosuroides, Apera spica-venti, Poa annua, Poa trivialis, Echinochloa crus-galli,* and *Digitaria sanguinalis* when applied prior to their emergence in the crop.

Therefore the said combined use represents an important technological advance.

Surprisingly, in addition to this, it has been found that the combined herbicidal activity of diflufenican with the HBN herbicide against many weed species is much greater than expected when applied post-emergence (e.g. as a post-emergence spray), i.e. the herbicidal activity of diflufenican with the HBN herbicide showed an unexpected and remarkable degree of synergism on many weed species, for example on *Setaria viridis*, as defined by P. M. L. Tammes, Netherlands Journal of Plant Pathology, 70 (1964), pp. 73–80 in a paper entitled "Isoboles, a graphic representation of synergism in pesticides", and on *Veronica hederifolia, Anthemis cotula, Vicia sativa, Epilobium paniculatum, Lamium amplexicaule, Montia linearis* and *Sisymbrium altissimum* as defined by Limpel, L. E., P. H. Schuldt, and D. Lamont, 1962, Proc. NEWCC 16:48–53, using the formula:

$$E = X + Y - \frac{XY}{100}$$

where
E = the expected percent inhibition of growth by a mixture of two herbicides at defined doses.
X = the percent inhibition of growth by herbicide A at a defined dose
Y = the percent inhibition of growth by herbicide B at a defined dose (when the observed response is greater than expected the combination is synergistic).

The remarkable synergistic effect of the mixture applied post-emergence gives improved reliability of control of a large number of weed species occurring in cereal culture and permits a reduction in the amount of active ingredient employed.

Accordingly the present invention provides a method for the control of the growth of weeds at a cereal crop locus which comprises the combined use of (a) bromoxynil, which is 3,5-dibromo-4-hydroxybenzonitrile, or ioxynil, which is 4-hydroxy-3,5-diiodobenzonitrile, an agriculturally acceptable salt or ester thereof, preferably a metal or amine salt or an ester thereof with an alkanoic acid containing from 2 to 10 carbon atoms, or a mixture, preferably a 3:1–1:3 wt/wt mixture calculated in terms of acid equivalent weights, thereof and (b) diflufenican, which is N-(2,4-difluorophenyl)-2-(3-trifluoromethylphenoxy)nicotinamide. Preferably the application rates of (a) and (b) are between 100 and 500 g acid equivalent (a.e.)/ha and between 25 and 250 g/ha respectively in proportions of 20:1 to 2:5 and preferably 8:1 to 1:1 wt/wt of (a) to (b). The method of the invention may be used to control a broad spectrum of weed species in cereal crops, e.g. wheat, barley, rice and maize, by pre- or post-emergence application, more especially early post-weed emergence post-crop emergence without significant permanent damage to the crop. The combined use described above offers both foliar and residual activity.

By the term 'pre-emergence application' is meant application to the soil in which the weed seeds or seedlings are present before emergence of the weeds above the surface of the soil. By the term 'post-emergence application' is meant application to the aerial or exposed portions of the weeds which have emerged above the surface of the soil. It will be appreciated that application according to the method may be from pre- to post-weed emergence pre-crop emergence to post-weed post-crop emergence. By the term 'foliar activity' is meant herbicidal activity produced by application to the aerial or exposed portions of the weeds which have emerged above the surface of the soil. By the term 'residual activity' is meant herbicidal activity produced by application to the soil in which weed seeds or seedlings are present before emergence of the weeds above the surface of the soil, whereby seedlings present at the time of application or which germinate subsequent to application from seeds present in the soil, are controlled.

In the method according to the present invention, the use of one or more of the esters as hereinbefore defined of the HBN herbicide is preferred. Of the HBN herbicide esters, those with alkanoic acids containing from 4 to 8 carbon atoms, and more particularly the octanoates or heptanoates or mixtures thereof, are preferably used. The use of bromoxynil octanoate or heptanoate or a mixture thereof is especially preferred.

Weeds that may be controlled by the method include: from broad-leaf weeds, Aethusa cynapium, Abutilon theophrasti, Amananthus retroflexus, Amsinckia intermedia, Anagallis arvensis, Anthemis arvensis, Anthemis cotula, Atriplex patula, Bidens pilosa, Brassica nigra, Capsella bursa-pastoris, Chenopodium album, Chrysanthemum segetum, Cirsium arvense, Datura stramonium, Desmodium tortuosum, Emex australis, Epilobium paniculatum, Euphorbia helioscopia, Fumaria officinalis, Galeopsis tetrahit, Galium aparine, Geranium dissectum, Ipomea purpurea, Lamium amplexicaule, Lamium purpureum, Lapsana communis, Matricaria inodora, Monochoria vaginalis, Montia linearis, Papaver rhoeas, Physalis longifolia, Plantago lanceolata, Polygonum spp. (e.g. Polygonum aviculare, Polygonum convolvulus and Polygonum persicaria), Portulaca oleracea, Raphanus raphanistrum, Rotala indica, Rumex obtusifolius, Saponaria vaccaria, Scandix pecten-veneris, Senecio vulgaris, Sesbania florida, Sida spinosa, Silene alba, Sinapis arvensis, Sisymbrium altissimum, Solanum nigrum, Sonchus arvensis, Spergula arvensis, Stellaria media, Thlaspi arvense, Tribulus terrestria, Urtica urens, Veronica hederifolia, Veronica persica, Vicia sativa, Viola arvensis and Xanthium strumarium, and from grass weeds, Alopecurus myosuroides, Apera spica-venti, Agrostis stolonifera, Poa annua, Poa trivalis, Digitaria sanguinalis, Echinochloa crus-galli, Eleusine indica, Setaria viridis and, from sedges, Cyperus iria and Eleocharis acicularis.

The pattern of persistence of the HBN herbicide and the diflufenican allow the method of the present invention to be practised by the time-separated application of separate formulations.

In accordance with usual practice, a tank mix may be prepared prior to use by combining separate formulations of the individual herbicidal components.

BRIEF DESCRIPTION OF THE DRAWING

The drawing is a plot of an isobole according to Tammes.

The following Experiments illustrate the present invention:

EXPERIMENT 1

The following greenhouse experiment demonstrates the synergistic activity of the combined use of bromoxynil and diflufenican in controlling the growth of Setaria viridis.

Greenhouse experiment showing nature of biological synergism between bromoxynil and diflufenican A factorial experiment with 25 treatments was carried out to investigate the interaction of bromoxynil and diflufenican at a wide range of doses, i.e. bromoxynil triethylamine (Example 1 hereinafter) at 0, 125, 250, 500 and 1000 g a.e. (acid equivalent)/ha plus diflufenican (Example 2 hereinafter) at 0, 125, 250, 500 and 1000 g a.i./ha as indicated in the matrix below were applied at a spray volume rate of 260 l/ha to three replicate 9 cm diameter pots of John Innes No. 1 potting compost planted with 5 Setaria viridis seedlings at the 2 leaf stage. After spraying the pots were arranged in randomised blocks in a greenhouse watered as necessary and assessed for percentage phytotoxicity (compared with unsprayed plants) after three weeks (0=no effect, 100=complete destruction).

| | | bromoxynil triethylamine g a.e./ha | | | |
|---|---|---|---|---|---|
| Treatment(no.) | (1) | (6) | (11) | (16) | (21) |
| | 0 | 125 | 250 | 500 | 1000 |
| | (2) | (7) | (12) | (17) | (22) |
| | | 125 | 250 | 500 | 1000 |
| | 125 | + | + | + | + |
| | | 125 | 125 | 125 | 125 |
| | (3) | (8) | (13) | (18) | (23) |
| diflufenican | | 125 | 250 | 500 | 1000 |
| g a.i./ha | 250 | + | + | + | + |
| | | 250 | 250 | 250 | 250 |
| | (4) | (9) | (14) | (19) | (24) |
| | | 125 | 250 | 500 | 1000 |
| | 500 | + | + | + | + |
| | | 500 | 500 | 500 | 500 |
| | (5) | (10) | (15) | (20) | (25) |
| | | 125 | 250 | 500 | 1000 |
| | 1000 | + | + | + | + |
| | | 1000 | 1000 | 1000 | 1000 |

The results were as follows:

| | Bromoxynil triethylamine | | | | | |
|---|---|---|---|---|---|---|
| Diflufenican | 0 | 0 | 0 | 0 | 0 | % phytotoxicity |
| | 30 | 40 | 45 | 50 | 70 | |
| | 38 | 40 | 50 | 60 | 80 | |
| | 45 | 60 | 60 | 80 | 90 | |
| | 60 | 70 | 80 | 100 | 100 | |

From these results the ED50 values (effective dose giving 50% phytotoxicity) in grams per hectare was calculated graphically for diflufenican alone and with increasing rates of bromoxynil triethylamine. Bromoxynil triethylamine had no activity on its own. The ED50 values were as follows:

| | | ED50 g a.i./ha |
|---|---|---|
| Diflufenican (dif.) | | 625 |
| dif. + bromoxynil | 125 g/ha | 325 |
| " | 250 g/ha | 225 |
| " | 500 g/ha | 150 |
| " | 1000 g/ha | 75 |

The results were then used to plot an isobole with a "one sided effect" according to P. M. L. Tammes, Netherlands Journal of Plant Pathology 70, 1964, pp. 73-80, Isoboles, a graphic representation of synergism in pesticides. The isobole produced was clearly a type II curve (Tammes, page 74 FIG. 1) characteristic of synergism (FIG. (i) hereinafter).

EXPERIMENT 2

A winter wheat crop at the 3-5 leaf stage contaminated with Veronica hederifolia at the 10-16 leaf stage was sprayed with bromoxynil octanoate (formulation Example 4) at 0.25 lb a.e./acre (0.28 kg a.e./hectare), diflufenican (formulation Example 2) at 0.125 lb a.i./acre (0.14 kg a.i./hectare) and a tank mix of the two in 20 g.p.a. (225 liter/ha). Treatments were applied to four replicate 8'×25' (2.4 m×7.6 m) randomised plots. 47 days after spraying percent injury to the crop and percent control of the weed was assessed. The mean result is given below.

| Treatment | | % crop injury | % control of Veronica hederifolia |
|---|---|---|---|
| bromoxynil octanoate | 0.25 lb a.e./ac (0.28 kg a.e./ha) | 0 | 15 |
| diflufenican | 0.125 lb a.i./ac (0.14 kg a.i./ha) | 0 | 60 |
| brom. oct. + dif. | 0.25 + 0.125 lb/ac (0.28 + 0.14 kg/ha) | 0 | 94 |

Using Limpel formula: $E = X + Y - \frac{XY}{100}$ $E = 15 + 60 - \frac{900}{100} = 66$ As the observed response on *Veronica hederifolia* was much higher than the expected the combination was clearly synergistic.

The crop tolerance was excellent.

EXPERIMENT 3

A winter wheat crop at the 2-3 leaf stage infested with *Anthemis cotula* (2-6 leaf), *Vicia sativa* (2-4 leaf) and *Epilobium paniculatum* (2-6 leaf) was treated in a similar manner to Experiment 2 and assessed for crop injury and weed control after 47 days. Results (mean of four replicates) were as follows:

| | % crop injury | Anthemis | % control Vicia | Epilobium |
|---|---|---|---|---|
| bromoxynil octanoate 0.25 lb/ac (0.2 kg/ha) | 0 | 15 | 0 | 3 |
| diflufenican 0.125 lb/ac(0.14 kg/ha) | 0 | 43 | 80 | 75 |
| brom. oct. + dif. 0.25 + 0.125 lb/ac (0.28 + 0.14 kg/ha) | 0 | 98 | 99 | 100 |

Expected control for Anthemis, Vicia and Epilobium using the Limpel formula was 52, 80 and 76 respectively, clearly demonstrating that the combination was synergistic. The crop tolerance was excellent.

EXPERIMENT 4

A winter wheat crop at the 4-6 leaf stage infested with *Lamium amplexicaule* (4-10 leaf), *Montia linearis* (6-10 leaf) and *Sisymbrium altissimum* (4-8 leaf) was treated in a similar manner to Experiment 2 and assessed for crop injury and weed control 41 days after spraying. Results (mean of four replicates) were as follows:

| | % crop injury | Lamium | % control Montia | Sisymbrium |
|---|---|---|---|---|
| bromoxynil octanoate 0.25 lb/ac (0.2 kg/ha) | 0 | 15 | 13 | 63 |
| diflufenican 0.125 lb/ac(0.14 kg/ha) | 0 | 23 | 18 | 18 |
| brom. oct. + dif. 0.25 + 0.125 lb/ac (0.28 + 0.14 kg/ha) | 0 | 94 | 97 | 99 |

Expected values for Lamium, Montia and Sisymbrium were 34, 29 and 70 respectively, thus the mixture was clearly synergistic. Crop tolerance was excellent.

EXPERIMENT 5

The efficacy of these synergistic mixtures for broad spectrum weed control in spring wheat and barley was demonstrated in small plot field trials where a combination of bromoxynil ester and diflufenican was compared with bromoxynil ester and with diflufenican alone. Diflufenican (Example 2 hereinafter) at 150 g a.i./ha, bromoxynil octanoate (commercial formulation) at 210 g a.e./ha and a tank mix of the two was applied in 102.9 liters/ha to 2 wheat and 1 barley crop at the 2-5 leaf stage. Treatments were applied to three replicate 17.5-25 m² plots using a motorised plot sprayer. Assessments of efficacy against weeds and safety to the crop were made visually two weeks after application using the following scale:

| RATING SCALE (ECW Western Canada) 1983 | |
|---|---|
| Weed Control | Crop Tolerance |
| 9 complete control — commercially acceptable | 9 complete tolerance |
| 8 excellent control | 8 possible effect |
| 7 good control | 7 slight effect |
| 6 fair control | 6 definite effect |
| 5 poor control | 5 severe effect |
| 4 moderate injury | 4 severe effect |
| 3 definite effect | 3 severe effect |
| 2 slight effect | 2 severe effect |
| 1 possible effect | 1 severe effect |
| 0 no effect | 0 complete kill |

The results are shown in Table I below.

TABLE I

| | Mean weed control and crop safety ECW Scales | | | | | | |
|---|---|---|---|---|---|---|---|
| Treatment | Setaria viridis | Thlaspi arvense | Chenopodium album | Fagopyrum tartaricum | Amaranthus retrofluxus | Wheat | Barley |
| Diflufenican 150 g a.i./ha | 4.8 | 5 | 1 | 0 | 6 | 9 | 9 |
| Diflufenican 150 g a.i./ha + Bromoxynil octanoate 210 g a.e./ha | 8.8 | 9 | 9 | 9 | 9 | 9 | 9 |
| Bromoxynil octanoate 210 g a.e./ha | 2.1 | 7.8 | 9 | 8 | 7.3 | 9 | 9 |
| Occurrences (no.) | 2 | 1 | 2 | 1 | 1 | 2 | 1 |

EXPERIMENT 6

The efficacy of these mixtures for control of *Galium aparine, Veronica hederifolia* and *Viola tricolor* was demonstrated in the following field trials where a bromoxynil ester/diflufenican tank mix was compared with bromoxynil ester alone.

Bromoxynil octanoate (commercial product) at 250 g a.e./ha and a tank mix of bromoxynil octanoate plus 150 g a.i./ha of diflufenican (Example 2 hereinafter) was applied at a volume rate of 330–500 l/ha to replicate small plots (15–30 m²) of 2 winter wheat and 2 winter barley crops using a knapsack sprayer. Weed control and crop safety are assessed as percentage phytotoxicity compared with untreated plots 20–30 days post spray.

The results are shown in Table II below.

TABLE II

| Treatment | Mean % phytotoxicity | | | | |
|---|---|---|---|---|---|
| | Galium aparine | Veronica hederifolia | Viola tricolor | Winter wheat | Winter barley |
| Bromoxynil octanoate 250 g a.e./ha | 70 | 7 | 47 | 1 | 1 |
| Bromoxynil 250 g a.3./ha + diflufenican 150 g a.i./ha | 95 | 82 | 98 | 1 | 3 |
| Occurrences | 1 | 2 | 2 | 2 | 2 |

EXPERIMENT 7

The efficacy of these mixtures is demonstrated in the following field trials where a bromoxynil potassium salt (Example 3 hereinafter) plus diflufenican (Example 2 hereinafter) tank mix was compared with diflufenican alone.

One winter wheat and 3 winter barley sites were treated post-emergence with diflufenican at 125 g a.i./ha and a tank mix of diflufenican at 125 g a.i./ha plus bromoxynil K salt at 300 g a.e./ha applied in 220–235 liters of spray fluid per hectare using a motorised small plot sprayer. Three replicate plots 30 m² were sprayed with each treatment at each site.

Weed control was assessed in late spring following early spring and winter application by counting the number of weeds occurring in 2×0.5 m² quadrats per plot and expressing control as percentage reduction in weed numbers compared with unsprayed plots. Crop safety was assessed visually using a 0–100% phytotoxicity scoring system (0%=no effect, 100% complete destruction).

The results are shown in Table III below.

of acid equivalent weights, thereof and (b) diflufenican in proportions of preferably 20:1 to 2:5 wt/wt of (a) to (b) [preferably 8:1 to 1:1 wt/wt of (a) to (b)] in association with, and preferably homogeneously dispersed in, one or more compatible herbicidally-acceptable diluents or carriers and/or surface-active agents (i.e. diluents or carriers or surface-active agents of the type generally accepted in the art as being suitable for use in herbicidal compositions and which are compatible with the HBN herbicide and diflufenican). The term "homogeneously dispersed" is used to include compositions in which the HBN herbicide and diflufenican are dissolved in the other components. The term "herbicidal compositions" is used in a broad sense to include not only compositions which are ready for use as herbicides but also concentrates which must be diluted before use. Preferably, the compositions contain from 0.05 to 90% by weight of the HBN herbicide and diflufenican.

The herbicidal compositions may contain both a diluent or carrier and a surface-active (e.g. wetting, dispersing, or emulsifying) agent. Surface-active agents which may be present in herbicidal compositions of the present invention may be of the ionic or non-ionic types, for example sulphoricinoleates, quaternary ammonium derivatives, products based on condensates of ethylene oxide with nonyl- or octyl-phenols, or carboxylic acid esters of anhydrosorbitols which have been rendered soluble by etherification of the free hydroxy groups by condensation with ethylene oxide, alkali and alkaline earth metal salts or sulphuric acid esters and sulphonic acids such as dinonyl- and dioctyl-sodium sulphonosuccinates and alkali and alkaline earth metal salts of high molecular weight sulphonic acid derivatives such as sodium and calcium lignosulphonates. Examples of suitable solid diluents or carriers are aluminium silicate, talc, calcined magnesia, kieselguhr, tricalcium phosphate, powdered cork, adsorbent carbon black and clays such as kaolin and bentonite. The solid compositions (which may take the form of dusts, granules or wettable powders) are preferably prepared by grinding the HBN herbicide and diflufenican with solid diluents or by impregnating the solid diluents or carriers with solutions of the HBN herbicide and diflufenican in volatile solvents, evaporating the solvents and, if necessary, grinding the products so as to obtain powders. Granular formulations may be prepared by absorbing the HBN herbicide and diflufenican (dissolved in volatile sol-

TABLE III

| Treatment | % control of weed numbers | | | | | | | | | crop phytotoxicity Winter | |
|---|---|---|---|---|---|---|---|---|---|---|---|
| | Poa annua | Stellaria media | Veronica persica | Viola arvensis | Cerastium arvensis | Capsella bursa-pastoris | Legousia hybrida | Matricaria inodora | Papaver rhoeas | wheat | barley |
| diflufenican 125 g a.i./ha | 69 | 90 | 95 | 90 | 100 | 100 | 99 | 44 | 66 | 0 | 0.83 |
| diflufenican 125 g a.i./ha + bromoxynil K salt 300 g a.e./ha | 86 | 96 | 99 | 98 | 100 | 100 | 100 | 95 | 98 | 0 | 1.38 |
| Occurrences | 2 | 3 | 3 | 2 | 1 | 1 | 1 | 1 | 2 | 1 | 3 |

According to a further feature of the present invention, there are provided compositions suitable for herbicidal use comprising (a) 3,5-dibromo-4-hydroxybenzonitrile or 4-hydroxy-3,5-diiodobenzonitrile, an agriculturally acceptable salt or ester thereof, preferably a metal or amine salt or an ester thereof with an alkanoic acid containing from 2 to 10 carbon atoms, or a mixture, preferably a 3:1–1:3 wt/wt mixture calculated in terms vents) onto the solid diluents or carriers in granular form and evaporating the solvents, or by granulating compositions in powder form obtained as described above. Solid herbicidal compositions, particularly wettable powders, may contain wetting or dispersing agents (for example of the types described above), which may also, when solid, serve as diluents or carriers.

Liquid compositions according to the invention may take the form of aqueous, organic or aqueous-organic solutions, suspensions and emulsions which may incorporate a surface-active agent. Suitable liquid diluents for incorporation in the liquid compositions include water, acetophenone, cyclohexanone, N-methylpyrrolidone, isophorone, toluene, xylene and mineral, animal and vegetable oils (and mixtures of these diluents). Surface-active agents, which may be present in the liquid compositions, may be ionic or non-ionic (for example of the types described above) and may, when liquid, also serve as diluents or carriers.

Wettable powders and liquid compositions in the form of concentrates may be diluted with water or other suitable diluents, for example mineral or vegetable oils, particularly in the case of liquid concentrates in which the diluent or carrier is an oil, to give compositions ready for use. When desired, liquid compositions of the HBN herbicide and diflufenican may be used in the form of self-emulsifying concentrates containing the active substances dissolved in the emulsifying agents or in solvents containing emulsifying agents compatible with the active substances, the simple addition of water to such concentrates producing compositions ready for use.

Liquid concentrates in which the diluent or carrier is an oil may be used without further dilution using the electrostatic spray technique.

Herbicidal compositions according to the present invention may also contain, if desired, conventional adjuvants such as adhesives, protective colloids, thickeners, penetrating agents, stabilisers, sequestering agents, anti-caking agents, colouring agents and corrosion inhibitors. These adjuvants may also serve as carriers or diluents.

Preferred herbicidal compositions according to the present invention are aqueous suspension concentrates which comprise from 10 to 70% w/v of the HBN herbicide and diflufenican, from 2 to 10% w/v of surface-active agent, from 0.1 to 5% w/v of thickener and from .15 to 87.9% by volume of water; wettable powders which comprise from 10 to 90% w/w of the HBN herbicide and diflufenican, from 2 to 10% w/w of surface-active agent and from 10 to 88% w/w of solid diluent or carrier; liquid water soluble concentrates which comprise from 10 to 30% w/v of the HBN herbicide and diflufenican, from 5 to 25% w/v of surface-active agent and from 45 to 85% by volume of water-miscible solvent, e.g. dimethylformamide or N-methylpyrrolidone; liquid emulsifiable suspension concentrates which comprise 10 to 70% w/v of the HBN herbicide and diflufenican, from 5 to 15% w/v of surface-active agent, from 0.1 to 5% w/v of thickener and from 10 to 84.9% by volume of organic solvent; granules which comprise from 2 to 10% w/w of the HBN herbicide and diflufenican, from 0.5 to 2% w/w of surface-active agent and from 88 to 97.5% w/w of granular carrier and emulsifiable concentrates which comprise from 0.05 to 90% w/v, and preferably from 1 to 60% w/v, of the HBN herbicide and diflufenican, from 0.01 to 10% w/v, and preferably from 1 to 10% w/v, of surface-active agent and from 9.99 to 99.94%, and preferably from 39 to 98.99%, by volume of organic solvent.

Herbicidal compositions according to the present invention may also comprise the HBN herbicide and diflufenican in association with, and preferably homogeneously dispersed in, one or more other pesticidally active compounds and, if desired, one or more compatible pesticidally acceptable diluents or carriers, surface-active agents and conventional adjuvants as hereinbefore described. Examples of other pesticidally active compounds which may be included in, or used in conjunction with, the herbicidal compositions of the present invention include herbicides, for example to increase the range of weed species controlled, for example alachlor [N-chloro-2,6-diethyl-N-(methoxymethyl)acetanilide], asulam [methyl (4-aminobenzenesulphonyl)carbamate], alloxydim[Na (sodium salt of 2-(1-allyloxyaminobutylidine)-5,5-dimethyl-4-methoxycarbonylcyclohexane-1,3-dione], atrazine [2-chloro-4-ethylamino-6-isopropylamino-1,3,5-triazine], barban [4-chlorobut-2-ynyl N-(3-chlorophenyl)carbamate], benzoylprop-ethyl [ethyl N-benzoyl-N-(3,4-dichlorophenyl)-2-aminopropionate], butachlor [N-(butoxymethyl)-α-chloro-2,6-diethylacetanilide], butylate [S-ethyl N,N-diisobutyl (thiocarbamate)], carbetamide [D-N-ethyl-2-(phenylcarbamoyloxy)propionamide], chlorfenpropmethyl [methyl 2-chloro-2-(4-chlorophenyl)propionate], chlorpropham [isopropyl N-(3-chlorophenyl)carbamate], chlortoluron [N'-(3-chloro-4-methylphenyl)-N,N-dimethylurea], cyanazine [2-chloro-4-(1-cyano-1-methylethylamino)-6-ethylamino-1,3,5-triazine], cycloate [N'-cyclohexyl-N-ethyl-S-ethyl(thiocarbamate)], 2,4-D [2,4-dichlorophenoxyacetic acid], dalapon [2,2-dichloropropionic acid], 2,4-DB [4-(2,4-dichlorophenoxy)butyric acid], desmedipham [3-(ethoxycarbonylamino)phenyl N-phenylcarbamate], diallate [S-2,3-dichloroallyl-N,N-diisopropyl(thiocarbamate)], dicamba [3,6-dichloro-2-methoxybenzoic acid], dichlorprop [(±)-2-(2,4-dichlorophenoxy)propionic acid], diclofop [(RS)-2-[4-(2,4-dichlorophenoxy)phenoxy]propionic acid], difenzoquat [1,2-dimethyl-3,5-diphenyl-pyrazolium salts], dimefuron [4-[2-chloro-4-(3,3-dimethylureido)phenyl]-2-t-butyl-1,3,4-oxadiazolin-5-one], dinitramine [$N^1,N^1$-diethyl-2,6-dinitro-4-trifluoromethyl-m-phenylenediamine], diuron [N'-(3,4-dichlorophenyl)-N,N-dimethylurea], EPTC [S-ethyl N,N-dipropyl(thiocarbamate)], ethofumesate [2-ethoxy-2,3-dihydro-3,3-dimethylbenzofuran-5-yl methylsulphonate], flamprop-isopropyl [isopropyl (±)-2-(N-benzoyl-3-chloro-4-fluoroanilino)propionate], flamprop-methyl [methyl (±)-2-(N-benzoyl-3-chloro-4-fluoroanilino)propionate], fluometuron [N'-(3-trifluoromethylphenyl)-N,N-dimethylurea], isoproturon [N'-(4-isopropylphenyl)-N,N-dimethylurea], linuron [N'-(3,4-dichlorophenyl)-N-methoxy-N-methylurea], MCPA [4-chloro-2-methylphenoxyacetic acid], MCPB [4-(4-chloro-2-methylphenoxy)butyric acid], mecoprop [(±)-2-(4-chloro-2-methyl-phenoxy)propionic acid], metamitron [4-amino-3-methyl-6-phenyl-1,2,4-triazin-5(4H)-one], methabenzthiazuron [N-(benzothiazol-2-yl)-N,N'-dimethylurea], metribuzin [4-amino-6-t-butyl-3-(methylthio)-1,2,4-triazin-5(4H)-one], molinate [S-ethyl N,N-hexamethylene(-thiocarbamate)], oxadiazon [3-(2,4-dichloro-5-isopropoxyphenyl)-5-t-butyl-1,3,4-oxadiazolin-2-one], paraquat [1,1'-dimethyl-4,4'-bipyridylium salts], pebulate [S-propyl N-butyl-N-ethyl(thiocarbamate)], phenmedipham [3-(methoxy-carbonylamino)phenyl N-(3-methylphenyl)carbamate], prometryne [4,6-bisisopropylamino-2-methylthio-1,3,5-triazine], propachlor [α-chloro-N-isopropyl-acetanilide], propanil [N-(3,4-dichlorophenyl)-propionamide], propham [isopropyl N-phenylcarbamate], pyrazone [5-amino-4-chloro-2- phenylpyridazin-3(2H)-one], simazine [2-chloro-4,6-bisethylamino-1,3,5-triazine], TCA (trichloroacetic acid), thiobencarb [S-(4-chlorobenzyl)-N,N-diethylthiolcarbamate], triallate [S-2,3,3-trichloroallyl N,N-diisopropyl(thiocarbamate)], and trifluralin [2,6-dinitro-N,N-dipropyl-4-trifluoromethylaniline]; insecticides, e.g. carbaryl [naphth-1-yl N-methylcarbamate]; synthetic pyrethroids, e.g. permethrin and cypermethrin; and fungicides, e.g. 2,6-dimethyl-4-tridecyl-morpholine, methyl N-(1-butylcarbamoylbenzinidazol-2-yl) carbamate, 1,2-bis-(3-methoxy-carbonyl-2-thioureidolbenzene, isopropyl 1-carbamoyl-3-(3,5-dichlorophenyl)-hydantoin and 1-(4-chlorophenoxy)-3,3-dimethyl-1-(1,2,4-triazol-1-yl)-butan-2-one. Other biologically active materials which may be included in, or used in conjunction with, the herbicidal compositions of the present invention are plant growth regulators, e.g. succinamic acid, (2-chloroethyl)trimethylammonium chloride and 2-chloroethane-phosphonic acid; or fertilizers, e.g. containing nitrogen, potassium and phosphorus and trace elements known to be essential to successful plant life, e.g. iron, magnesium, zinc, manganese, cobalt and copper.

Pesticidally active compounds and other biologically active materials which may be included in, or used in conjunction with, the herbicidal compositions of the present invention, for example those hereinbefore mentioned, and which are acids, may, if desired, be utilized in the form of conventional derivatives, for example alkali metal and amine salts and esters.

Preferred herbicidal compositions according to the present invention which comprise the HBN herbicide and diflufenican in association with another herbicide are those wherein the other herbicide is diclofop, MCPA or mecoprop or an agriculturally acceptable salt or ester thereof.

According to a further feature of the present invention there is provided a method according to the present invention as hereinbefore described in which in addition diclofop, MCPA or mecoprop or an agriculturally acceptable salt or ester thereof is applied preferably at an application rate of between 500 and 1500 g a.e./ha; between 100 and 1500 g a.e./ha and between 1000 and 2500 g a.e./ha respectively (preferably between 570–1140 g a.e./ha, between 150 and 1000 g a.e./ha and between 1000 and 2000 g a.e./ha respectively) for weed control in cereals, preferably small grain cereals, e.g. wheat and barley.

The compositions of the invention may be made up as an article of manufacture comprising the HBN herbicide and diflufenican and optionally other pesticidally active compounds as hereinbefore described or, as is preferred, a herbicidal composition as hereinbefore described, and preferably a herbicidal concentrate which must be diluted before use, comprising the HBN herbicide and diflufenican within a container for the aforesaid HBN herbicide and diflufenican or a said herbicidal composition, and instructions physically associated with the aforesaid container setting out the manner in which the aforesaid HBN herbicide and diflufenican or herbicidal composition contained therein is to be used to control the growth of weeds. The containers will normally be of the types conventionally used for the storage of chemical substances which are solids at normal ambient temperatures and herbicidal compositions, particularly in the form of concentrates, for example cans and drums of metal, which may be internally-lacquered, and plastics materials, bottles of glass and plastics materials and, when the contents of the container is a solid, for example granular herbicidal compositions, boxes, for example of cardboard, plastics materials and metal, or sacks. The containers will normally be of sufficient capacity to contain amounts of the active ingredients or herbicidal compositions sufficient to treat at least one acre of ground to control the growth of weeds therein but will not exceed a size which is convenient for conventional methods of handling. The instructions will be physically associated with the container, for example by being printed directly thereon or on a label or tag affixed thereto. The directions will normally indicate that the contents of the container, after dilution if necessary, are to be applied to control the growth of weeds at rates of application between 100 g and 500 g a.e. of the HBN herbicide and between 25 g and 250 g of diflufenican per hectare in the manner and for the purpose hereinbefore described.

According to a further feature of the present invention, there is provided a product comprising (a) 3,5-dibromo-4-hydroxybenzonitrile or 4-hydroxy-3,5-diiodobenzonitrile, an agriculturally acceptable salt or ester thereof, preferably a metal or amine salt or an ester thereof with an alkanoic acid containing from 2 to 10 carbon atoms, or a mixture, preferably a 3:1–1:3 wt/wt mixture calculated in terms of acid equivalent weights, thereof and (b) diflufenican as a combined preparation for simultaneous, separate or sequential use in controlling the growth of weeds at a cereal crop locus.

The following Examples illustrate herbicidal compositions according to the present invention and herbicidal compositions suitable for use in the method for controlling the growth of weeds according to the present invention.

EXAMPLE 1

A water-miscible composition containing bromoxynil triethylamine salt was prepared from:

| | |
|---|---|
| bromoxynil | 34% w/v |
| triethylamine | 15% w/v |
| Soprophor BSU (tristyryl phenol/ ethylene oxide condensate containing 18 moles of ethylene oxide | 1.5% w/v |
| diethylene glycol | 25% w/v |
| water | to 100% by volume | by mixing together a portion of the water, the diethylene glycol, the bromoxynil and the triethylamine (15% w/v of triethylamine represents a 2.6% by weight excess of triethylamine over the stoichiometric amount required to form bromoxynil triethylamine salt) with heating and stirring. The tristyryl phenol/ethylene oxide condensate was then added and the volume was made up to 100% by the addition of water.

EXAMPLE 2

| | |
|---|---|
| Diflufenican | 50% w/v |
| Ethylan BCP (a nonylphenol-ethylene oxide condensate containing 9 moles of ethylene oxide per mole of phenol) | 0.5% w/v |
| Soprophor FL (triethanolamine salt of oxyethylated polyarylphenolphosphate) | 1.0% w/v |
| Sopropon T36 (sodium polycarboxylate) | 0.5% w/v |
| Antifoam FD (silicone antifoam) | 0.1% w/v |
| Rhodigel 23 (xanthan gum) | 0.2% w/v |
| Dichlorophen sodium solution, 40% w/w | 0.25% w/v |
| Water | to 100% by |

EXAMPLE 3

A water-miscible composition containing bromoxynil potassium salt was prepared from:

| | |
|---|---|
| bromoxynil | 25% w/v |
| potassium hydroxide | 5.1% w/v |
| tetrahydrofurfuryl alcohol | 25% w/v |
| water | to 100% by volume | by mixing together a portion of the water, the tetrahydrofurfuryl alcohol, the bromoxynil and the potassium hydroxide with heating and stirring and then the volume was made up to 100% by the addition of water.

EXAMPLE 4

An emulsifiable composition containing bromoxynil octanoate was prepared from:

| | |
|---|---|
| bromoxynil octanoate containing 63.9% w/w phenol acid equivalent | 35.2% w/v |
| Atlox 4855 (a mixture of anionic and nonionic surfactants) | 3.75% w/v |
| Agrilan A (a mixture of anionic and nonionic surfactants) | 3.75% w/v |
| Solvesso 150 (aromatic C10 petroleum fraction) | to 100% by volume | by mixing together a portion of the aromatic C10 petroleum fraction, the Atlox 4855, the Agrilan A and the bromoxynil octanoate with heating and stirring and then the volume was made up to 100% by the addition of aromatic C10 petroleum fraction.

EXAMPLE 5

An aqueous suspension concentrate containing bromoxynil phenol was prepared from:

| | |
|---|---|
| bromoxynil | 56.25% w/v |
| Soprophor FL (phosphate ester of aryl phenol ethoxylate | 3.5% w/v |
| Sopropon T36 (sodium salt of polycarboxylic acid) | 0.3% w/v |
| Ethylan BCP (nonyl phenol/ethylene oxide condensate containing 9 moles of ethylene oxide) | 0.5% w/v |
| Antifoam FD (silicone antifoam) | 0.1% w/v |
| Attagel 50 (swellable attapulgite clay) | 2.0% w/v |
| propylene glycol | 5.0% w/v |
| water | to 100% by volume | by intimately mixing the ingredients and grinding by pumping under pressure through a bead-charged mill.

EXAMPLE 6

An aqueous suspension concentrate containing bromoxynil octanoate and diflufenican (5.87:1) was prepared from:

| | |
|---|---|
| bromoxynil octanoate containing 63.9% w/w phenol acid equivalent | 35.2% w/v |
| Arylan CA (calcium dodecyl benzene sulphonate 70% solution in butanol) | 2.0% w/v |
| Synperonic NPE 1800 (nonyl phenol ethylene oxide/propylene oxide block copolymer) | 3.0% w/v |
| Solvesso 200 (aromatic C10/C13 petroleum fraction) | 6.0% w/v |
| diflufenican | 6.0% w/v |
| Soprophor 3D33 (ethoxylated polyaryl phenol phosphate neutralised with triethanolamine) | 0.16% w/v |
| Olin 10G (nonyl phenol/glycidol condensate containing 10 moles of glycidol) | 0.08% w/v |
| Antifoam FD (silicone antifoam) | 0.2% w/v |
| Attagel 50 (swellable attapulgite clay) | 2.0% w/v |
| ammonium chloride | 5.0% w/v |
| water | to 100% by volume | by mixing together the calcium dodecyl benzene sulphonate solution, the nonyl phenol ethylene oxide/propylene oxide block copolymer, the aromatic C10/C13 petroleum fraction and the bromoxynil octanoate with heating and stirring. An aqueous suspension concentrate was then prepared by intimately mixing 40% by volume of water with the diflufenican, the ethoxylated polyaryl phenol phosphate neutralised with triethanolamine, the nonyl phenol/glycidol condensate, the silicone antifoam, the attapulgite clay and the ammonium chloride and then grinding by pumping under pressure through a bead-charged mill. The previously prepared bromoxynil octanoate solution was then added to this suspension concentrate with stirring and the volume was made up to 100% by the addition of water.

1.5 liters of the resulting formulation was diluted in 200 liters of water and sprayed post-emergence to control *Stellaria media, Viola arvensis* and *Veronica persica* in one hectare of winter wheat.

EXAMPLE 7

A 10:1 mixture was formed by tank mixing 888 ml of the composition of Example 5 with 100 ml of the composition of Example 2 in a volume of 100 liters of water. The resulting spray fluid was applied to one hectare of emerged barley to control *Polygonum convolvulus, Sinapis arvensis* and *Amaranthus retroflexus.*

EXAMPLE 8

A 20:1 mixture was formed by tank mixing 888 ml of the composition of Example 5 with 50 ml of the composition of Example 2 in a volume of 100 liters of water. The resulting spray fluid was applied to one hectare of emerged barley to control *Polygonum convolvulus, Sinapis arvensis* and *Amaranthus retroflexus.*

EXAMPLE 9

A 2:5 mixture was formed by tank mixing 444 ml of formulation of Example 4 with 500 ml of formulation of Example 2 in 300 liters of water. The resulting spray fluid was applied to one hectare of spring wheat soon after emergence to control emerged and germinating *Setaria viridis* and *Amaranthus retroflexus.*

EXAMPLE 10

A tank mix consisting of 600 ml of formulation of Example 6 and 1800 ml of a stable aqueous solution containing potassium, sodium and dimethylamine salts of MCPA equivalent to 500 g/l of 2-methyl-4 chlorophenoxyacetic acid was made in 200 liters of water. This was applied post-emergence to one hectare of winter wheat to control *Stellaria media, Galeopsis tetrahit, Sinapis arvensis* and *Viola arvensis*.

In the mixed formulations in the Examples hereinbefore, the HBN herbicide may be replaced by one other or a mixture of the HBN herbicides.

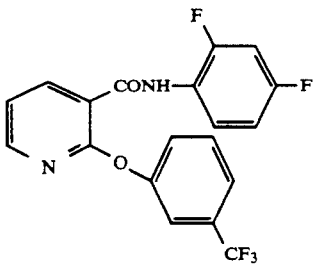

We claim:

1. A method of controlling the growth of weeds at a cereal crop locus which comprises applying to the locus an effective amount of (a) bromoxynil, which is 3,5-dibromo-4-hydroxy-benzonitrile, or ioxynil, which is 4-hydroxy-3,5-diiodobenzonitrile, an agriculturally acceptable salt or ester thereof or a mixture thereof and (b) diflufenican which is N-(2,4-difluorophenyl)-2-(3-trifluoromethylphenoxy)nicotinamide, in which the acid equivalent weight ratio of (a) to (b) is from 8:1 to 2:5 in which (a) is applied to the locus at a rate of from 100 to 500 g acid equivalent/ha and (b) at a rate of from 25 to 250 g/ha.

2. A method according to claim 1 in which the acid equivalent weight ratio of (a) to (b) is from 8:1 to 1:1.

3. A method according to claim 1, in which (a) comprises the ester of bromoxynil or ioxynil with an alkanoic acid of from 2 to 10 carbon atoms.

4. A method according to claim 3 in which (a) comprises the ester of bromoxynil or ioxynil with an alkanoic acid of from 4 to 8 carbon atoms.

5. A method according to claim 3 in which (a) comprises the ester of bromoxynil or ioxynil with octanoic or heptanoic acid.

6. A method according to claim 5 in which (a) comprises bromoxynil octanoate or bromoxynil heptanoate.

7. A method according to claim 1 in which (a) comprises a mixture of acid esters of bromoxynil or ioxynil.

8. A method according to claim 1 in which the application is early post-weed emergence post-crop emergence.

9. A method according to claim 1 in which the mixture of bromoxynil and ioxynil is in a ratio of 3:1–1:3 wt/wt calculated in terms of acid equivalent weights.

10. A product comprising an effective amount of (a) bromoxynil, which is 3,5-dibromo-4-hydroxybenzonitrile, or an agriculturally acceptable salt or ester thereof, or a mixture thereof, and (b) diflufenican, which is N-(2,4-difluorophenyl)-2-(3-trifluoromethylphenoxy)nicotinamide, in which the acid equivalent weight ratio of (a) to (b) is from 8:1 to 2:5 and the components (a) and (b) are capable of simultaneous or sequential use in controlling the growth of weeds at a cereal crop locus.

11. A product according to claim 10 in which (a) comprises the ester of bromoxynil or ioxynil with an alkanoic acid of from 2 to 10 carbon atoms.

12. A product according to claim 11 in which (a) comprises the ester of bromoxynil or ioxynil with an alkanoic acid of from 4 to 8 carbon atoms.

13. A product according to claim 11 in which (a) comprises the ester of bromoxynil or ioxynil with octanoic or heptanoic acid.

14. A product according to claim 13 in which (a) comprises bromoxynil octanoate or bromoxynil heptanoate.

15. A product according to claim 10 in which (a) comprises a mixture of acid esters of bromoxynil or ioxynil.

16. A product according to claim 10 in which the mixture of bromoxynil and ioxynil is in a ratio of 3:1–1:3 wt/wt calculated in terms of acid equivalent weights.

17. A herbicidal composition which comprises an effective amount of (a) bromoxynil or ioxynil or an agriculturally acceptable salt or ester thereof, or a mixture thereof, and (b) diflufenican in association with a herbicidally acceptable diluent or carrier and/or surface active agent in which the acid equivalent weight ratio of (a) to (b) is between 8:1 and 2:5.

18. A herbicidal composition according to claim 17 in which the acid equivalent weight ratio of (a) to (b) is between 8:1 and 1:1.

19. A herbicidal composition according to claim 17, in which (a) comprises the ester of bromoxynil or ioxynil with an alkanoic acid of from 2 to 10 carbon atoms.

20. A herbicidal composition according to claim 19 in which (a) comprises the ester of bromoxynil or ioxynil with an alkanoic acid of from 4 to 8 carbon atoms.

21. A herbicidal composition according to claim 19 in which (a) comprises the ester of bromoxynil or ioxynil with octanoic or heptanoic acid.

22. A herbicidal composition according to claim 21 in which (a) comprises bromoxynil octanoate or bromoxynil heptanoate.

23. A herbicidal composition according to claim 17 in which (a) comprises a mixture of acid esters of bromoxynil or ioxynil.

24. A herbicidal composition according to claim 17 which comprises from 0.05 to 90% by weight of diflufenican and bromoxynil or ioxynil or an agriculturally acceptable salt or ester thereof.

25. A herbicidal composition according to claim 17 in which the mixture of bromoxynil and ioxynil is in a ratio of 3:1–1:3 wt/wt calculated in terms of acid equivalent weights.

26. The method of claim 1, wherein (a) comprises bromoxynil or an agriculturally acceptable salt or ester thereof.

27. The method of claim 26, wherein the acid equivalent weight ratio of (a) to (b) is from 8:1 to 1:1.

28. The method of claim 26, wherein (a) comprises an ester of bromoxynil with an alkanoic acid of from 2 to 10 carbon atoms.

29. The method according to claim 28 in which (a) comprises the ester of bromoxynil with an alkanoic acid of from 4 to 8 carbon atoms.

30. The method according to claim 26 in which (a) comprises a mixture of acid esters of bromoxynil.

31. The method according to claim 26 in which the application is early post-weed emergence post-crop emergence.

32. The product of claim 10, wherein (a) comprises bromoxynil or an agriculturally acceptable salt or ester thereof.

33. The product according to claim 32 in which (a) comprises an ester of bromoxynil with an alkanoic acid of from 2 to 10 carbon atoms.

34. The product according to claim 33 in which (a) comprises an ester of bromoxynil with an alkanoic acid of from 4 to 8 carbon atoms.

35. The product according to claim 32 in which (a) comprises a mixture of acid esters of bromoxynil.

36. The herbicidal composition of claim 17, wherein (a) comprises bromoxynil or an agriculturally acceptable salt or ester thereof.

37. The herbicidal composition according to claim 36 in which the acid equivalent weight ratio of (a) to (b) is between 8:1 and 1:1.

38. The herbicidal composition according to claim 36 in which (a) comprises the ester of bromoxynil with an alkanoic acid of from 2 to 10 carbon atoms.

39. The herbicidal composition according to claim 38 in which (a) comprises the ester of bromoxynil with an alkanoic acid of from 4 to 8 carbon atoms.

40. The herbicidal composition according to claim 36 in which (a) comprises a mixture of acid esters of bromoxynil.

41. The herbicidal composition according to claim 36 which comprises from 0.05 to 90% by weight of diflufenican and bromoxynil or an agriculturally acceptable salt or ester thereof.

42. A method according to claim 1 wherein said weeds are selected from the group consisting of *Setaria viridis, Veronica hederifolia, Anthemis cotula, Vicia sativa, Epilobium paniculatum, Lamium paniculatum, Martia linearis, Sisymbrium altissimum* and mixtures thereof.

43. A method according to claim 42 wherein said weeds are controlled in post emergence application at a locus where a cereal crop is growing.

* * * * *